US006709390B1

(12) United States Patent
Marie Pop

(10) Patent No.: US 6,709,390 B1
(45) Date of Patent: Mar. 23, 2004

(54) METHOD, DEVICE AND CATHETER FOR IN VIVO DETERMINING BLOOD PROPERTIES SUCH AS BLOOD VISCOSITY

(75) Inventor: Gheorghe Aurel Marie Pop, Schiedam (NL)

(73) Assignee: Martil Instruments B.V. (NL)

( * ) Notice: Subject to any disclaimer, the term of this patent is extended or adjusted under 35 U.S.C. 154(b) by 30 days.

(21) Appl. No.: 09/600,290

(22) PCT Filed: Jun. 5, 2000

(86) PCT No.: PCT/NL00/00378

§ 371 (c)(1),
(2), (4) Date: Mar. 12, 2001

(87) PCT Pub. No.: WO00/74775

PCT Pub. Date: Dec. 14, 2000

(30) Foreign Application Priority Data

Jun. 3, 1999 (NL) .............................................. 1012223

(51) Int. Cl.⁷ ................................................. A61B 5/00
(52) U.S. Cl. ........................ 600/368; 600/369; 600/547
(58) Field of Search ............................. 600/368, 9, 547

(56) References Cited

U.S. PATENT DOCUMENTS

| 3,674,012 | A | * | 7/1972 | Sage .......................... 600/368 |
| 4,562,843 | A | * | 1/1986 | Djordjevich et al. ........ 600/547 |
| 5,305,745 | A | * | 4/1994 | Zacuoto ...................... 600/369 |
| 5,603,333 | A | * | 2/1997 | Konings ..................... 600/547 |
| 5,842,998 | A | * | 12/1998 | Gopakumaran et al. .... 600/547 |

FOREIGN PATENT DOCUMENTS

| EP | 0434856 | * | 7/1991 | ................. 600/547 |
| EP | 0647426 | * | 4/1995 | ................. 600/547 |
| EP | 0765671 | * | 4/1997 | ................. 600/547 |
| WO | 98/31421 | * | 7/1998 | ................. 600/547 |

* cited by examiner

Primary Examiner—Robert L. Nasser
(74) Attorney, Agent, or Firm—Mark Zovko

(57) ABSTRACT

The invention relates to a method for determining properties of blood, such as the blood viscosity of a person, comprising of generating in vivo for a determined time, by means of an electrical alternating current of a determined frequency, a measurement signal of the impedance of the blood between at least two points centrally in a blood volume, wherein the measurement signal is processed such that variations therein with a frequency in the order of magnitude of the heart frequency are substantially absent therefrom, and comparing the processed measurement signal with predetermined relations between impedance and the properties of the blood, such as the viscosity.

22 Claims, 2 Drawing Sheets

Figure 1:
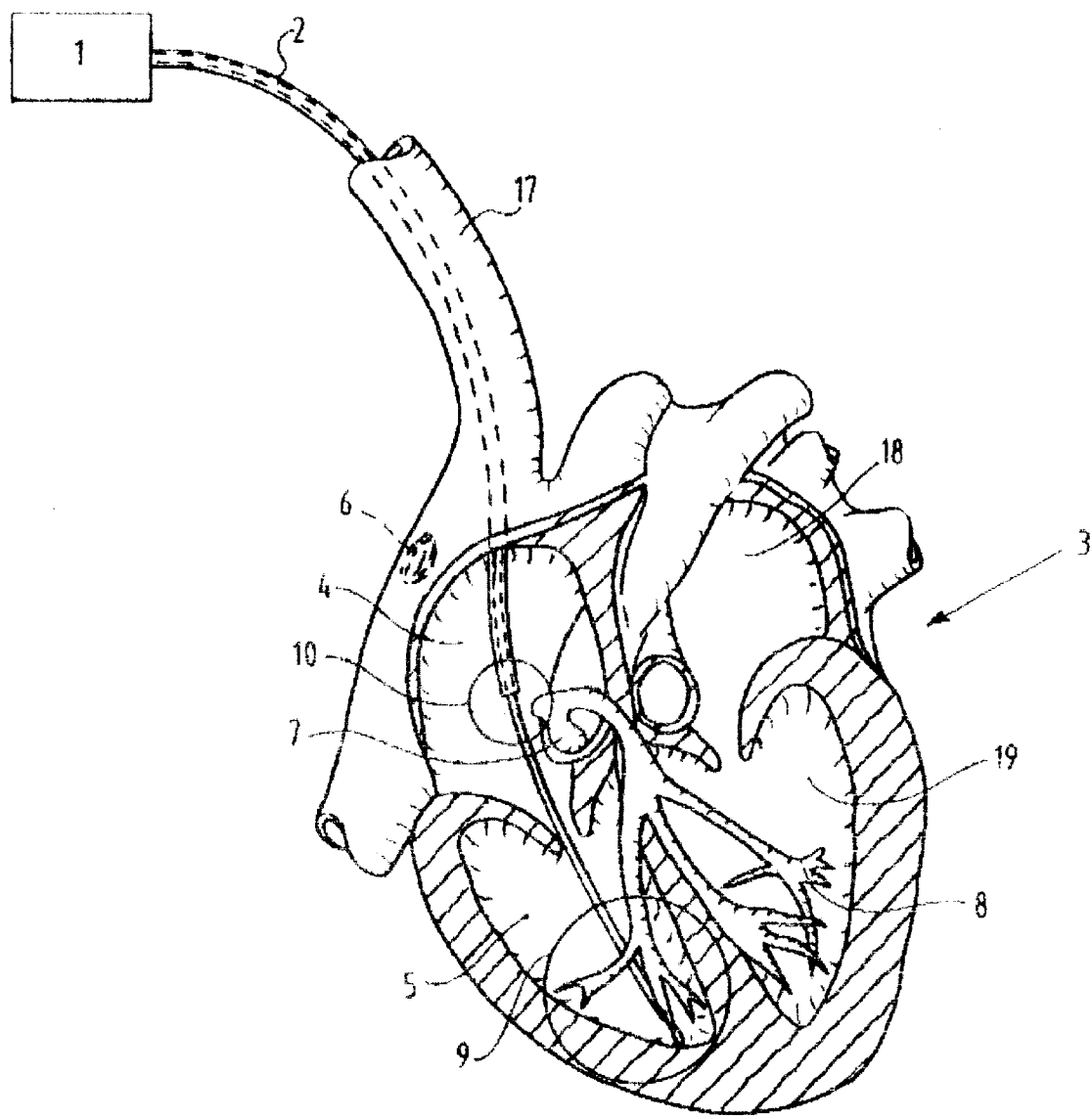

METHOD, DEVICE AND CATHETER FOR IN VIVO DETERMINING BLOOD PROPERTIES SUCH AS BLOOD VISCOSITY

The invention relates to a method for determining properties of blood, such as the blood viscosity of a person.

Atherosclerosis is the most common disease in the western world and partly for this reason represents one of the greatest problems with which our health care services and our society in general are confronted. Since atherosclerosis is clearly related to age, the problems associated with atherosclerosis will only increase due to the increase in the ageing population in the western world. Atherosclerosis is a generalized disease which can manifest itself in the coronaries by means of acute heart death, myocardial infarction or disabling angina pectoris. Atherosclerosis in the head is responsible for the largest number of strokes. Not only does this cause mortality, but also a greater or lesser degree of permanent invalidity. Elsewhere in the blood vessels of the body atherosclerosis can be the cause of reduced blood circulation in the legs or in the kidneys. Thrombosis is found to play an essential part in the process of atherosclerosis and increasingly recognized recently is also the significant part which inflammatory processes can play in activating and perhaps sometimes also in causing atherosclerosis. Much atherosclerosis therapy therefore focuses on suppressing thrombosis. It has also been found that the presence of "markers" of inflammation (such as CRP and other active-phase-proteins) entails an increased chance of atherosclerotic complications. The present invention has for its object to provide a method which enables monitoring of thrombosis processes and/or the activity of atherosclerosis. The prevention of atherosclerotic complications can hereby be controlled better and the medicinal therapy (anti-thrombotic and anti-inflammatory) can be adapted thereto.

It is known that the risk of thrombosis and atherosclerotic complications increases with an increase in the viscosity of the blood. The taking of blood so as to determine the viscosity is however time-consuming and costly, particularly when this has to be determined over a longer time and regularly in order to monitor the risks for a patient. Furthermore, when blood is taken for examination in vitro, the viscosity and coagulation parameters of blood are influenced to a certain extent and do not therefore give an accurate representation of the properties of blood in vivo. They are also only random indications which can be influenced by many factors and thus provide only limited certainty that, if necessary, timely treatment can be undertaken as the risk increases.

The invention therefore has for its object to provide a method of the type specified in the preamble which at least reduces these drawbacks.

In the method according to the invention this object is achieved by generating in vivo for a determined time, by means of an electrical alternating current of a determined frequency, a measurement signal of the impedance of the blood between at least two points centrally in a blood volume, wherein the measurement signal is processed such that variations therein with a frequency in the order of magnitude of the heart frequency are substantially absent therefrom, and comparing the processed measurement signal with predetermined relations between impedance and the properties of the blood, such as the viscosity. A continuously determined impedance measurement signal varies with ambient parameters such as the flow speed. By eliminating the variations with a frequency in the order of magnitude of the heart frequency a reliable value is obtained for the actual blood properties such as the viscosity, and thus the risks for the patient.

An ECG signal is further measured in a cavity containing the blood volume and processing of the measurement signal occurs by only considering measurement values in the same phase as the ECG signal. The phase of the ECG signal corresponds to the maximal and/or minimal impedance. By measuring each time in the same phase of the heart rhythm, the conditions for the flow speed and the like are the same each time, so that the variations with the frequency of the heart rhythm are eliminated. The energy consumption is moreover low herein, so that the device can operate on batteries and can for instance be portable.

According to a further development of the invention a blood viscosity reducing agent is applied to the patient in a dosage such that the measured impedance is reduced to a predetermined value. Precise determining of the viscosity enables a good dosing of the agent.

The distance between the aforementioned two points centrally in the blood volume is a small fraction of the distance between the two points and the boundary of the blood volume. In this way, the measurement is influenced by surrounding tissue to a negligible extent at most.

A good measurement is obtained particularly when the aforementioned two points are located centrally in the right atrium of the heart of the patient is applied. The right-hand atrium is readily accessible for the measurement and comprises a suitably large volume of blood to enable a precise measurement.

The invention likewise relates to and provides a device for in vivo determining of determined blood properties, such as the blood viscosity of a person, comprising a catheter, which comprises at least two electrode systems close to a distal end and connecting lines extending from the electrode systems to the proximal end of the catheter, a measuring device which is connectable to the connecting lines and which is embodied such that it can generate a measurement signal of the impedance between the electrode systems, and a processing device which is embodied such that it processes the measurement signal such that variations therein with a frequency in the order of magnitude of the heart frequency are substantially absent therefrom.

According to a suitable embodiment the measuring unit of the device according to the invention is received in an implantable unit. After introduction into a patient the progress of the measured blood property can be monitored regularly for a longer period of time. The device according to the invention can however also be used for more short-term applications, for instance in the case of acute thrombotic events, in which case the measuring device and the processing device are received in housings which remain outside the body of the patient. The catheter introduced into the patient via a peripheral vein is connected to the measuring device.

According to a very suitable embodiment the measuring device is combined with an implantable heart pacemaker unit and provided with two electrically separated circuits each having an individual power source, wherein the one circuit is adapted for the pacemaker function and the other circuit is adapted for the impedance measurement.

Heart pacemakers are generally known. The pacemaker unit herein contains, as can also be the case in the invention, an electrical power supply generally in battery form and the electronics required for the pacemaker function. The pacemaker unit is further also often provided with read-out means so that radiographic data can be read out in order to enable monitoring of the operation of the pacemaker and thus also the patient. The pacemaker unit is generally implanted on the chest under the skin. The device according to the invention, whether or not combined with a heart pacemaker, can be introduced in the same manner.

An electric catheter, referred to as the "lead" in professional jargon, is fixed to the device according to the invention when it is implanted under the skin. This electric catheter is inserted into the bloodstream at a suitable location and guided via the bloodstream to the heart. One or more electrodes are then placed on the electric catheter, generally on the end thereof. Via these electrodes it is then possible to generate an electrical stimulus which supports the working of the heart. As is generally known, current pulses in the order of 5 mA for 0.5 ms are herein generally more than sufficient. In older models of pacemakers a stimulus signal is generated at a fixed frequency. In the pacemakers substantially employed nowadays, so-called "on demand pacemakers", a further sensor is however provided on the so-called lead. This sensor monitors whether the heart is functioning properly.

Subject to the sensor signal, the heart pacemaker unit will be able to decide whether or not a stimulus signal must be generated via a stimulating electrode. It is conceivable here for the sensor electrode and stimulating electrodes to be formed by one and the same electrode or to be integrated into one electrode.

It is per se known that blood has electrical properties and that these electrical properties are different for the plasma and the blood cells. The plasma and the interior of the blood cells consist of conductive fluids with a determined electrical resistance, and the cell membranes consist of phospholipids and proteins with dielectric properties. The electrical impedance of blood is thus primarily determined by three parameters: the plasma resistance, the interior resistance in the cell and the capacitance of the membrane.

The electrical impedance of blood is found to change in the presence of coagulation factors such as fibrinogen. The electrical impedance of blood is also found to be closely related to the erythrocyte sedimentation rate, which is a significant "marker" for the extent of an inflammatory process. A measured impedance of the blood can be related to a so-called thrombosis factor, which provides a measure for the tendency to thrombosis, and to a factor which indicates the extent of inflammation in atherosclerosis. These factors can then be linked to a medication to prevent these processes. The factors can then for instance be linked to a determined dosage of a particular medicine. It will be apparent that the measured impedance can optionally also be linked directly to a medication or a determined dosage of a particular medicine. It will generally be the case that the lower the intravascularly measured electrical resistance of the blood, the smaller the chance of thrombosis and the lower the inflammatory activity of the atherosclerosis. In addition, it will generally be the case that the chance of thrombosis increases when the measured electrical capacitance of the blood increases. It will however be apparent that these are basic principles, exceptions to which can be envisaged.

In accordance with a particular embodiment, the device according to the invention is further adapted to determine a factor subject to the measured impedance, which factor is a measure for the tendency to thrombosis and/or the device is further adapted to determine a factor subject to the measured impedance, which factor indicates the inflammatory activity in atherosclerosis.

By means of test measurements, for instance in a laboratory outside the human body, it is possible to determine a more or less precise relation between the electrical impedance of the blood on the one hand and the chance of thrombosis and/or the atherosclerotic activity on the other, in order to thus assign to this chance respectively activity a factor which will take on a greater value as the chance respectively activity increases (it should however be noted that it is also conceivable to have the value of the thrombosis factor decrease with the chance respectively activity).

According to the invention the impedance measurement can in particular relate to either a resistance measurement or a capacitance measurement or a phase difference measurement, or a combination of these. Which of these types of impedance measurement is applied can be patient-dependent and/or can depend on the type of thrombosis formation it is wished to monitor.

In order to prevent the impedance measurement possibly disrupting the actual pacemaker function, it is advantageous according to the invention when the device, if it is combined with a heart pacemaker unit, is provided with two electrically separated circuits each having an individual power source, wherein the one circuit is adapted for the pacemaker function and the other circuit is adapted for the intravascular impedance measurement.

It is particularly advantageous according to the invention when the intravascular part is embodied such that the at least two electrodes can be placed in the right-hand atrium of the heart for performing the impedance measurement. This is advantageous according to the invention because the electrodes will be placed as freely as possible in the blood without contact with other tissue, whereby the impedance of the blood per se is measured. For the connection between the pacemaker unit and the intravascular part with the electrodes for the intravascular impedance measurement it is important that this connection enables the transfer of signals between the pacemaker unit and the electrodes.

As it is of particular practical advantage when the electrical power supply is accommodated in the unit, as is usual as such in pacemakers, it is recommended that the connection be an electrical connection, in which case the device according to the invention will comprise a catheter, in professional jargon the so-called lead, which is connected on the one hand to the device and on the other to the intravascular part, wherein the intravascular part as such can form part of the catheter.

Taking this into consideration, the device according to the invention comprises in a preferred embodiment a catheter which comprises an intravascular part with at least two electrode systems for impedance measurement, is electrically connectable with one end to the pacemaker unit, and comprises one or more sensor electrodes and/or stimulating electrodes for the pacemaker function.

A further, more advantageous embodiment of the above described embodiment with electric catheter, intended for a device combined with a heart pacemaker, provides that the sensor electrodes and/or stimulating electrodes for the pacemaker function are arranged at the other end of the catheter, that the other end of the catheter is intended for placing in the apex of the right-hand ventricle, and that the distance between this other end of the catheter on the one hand and the intravascular part with the electrodes for the impedance measurement on the other is such that when the other end is placed in the apex of the right-hand ventricle, the intravascular part is situated in the right-hand atrium.

According to a further advantageous embodiment, the device is adapted to enable remote read-out of the determined factors of thrombosis formation and/or of inflammatory activity and/or the measured impedance values. This read-out can then take place on-line for instance for 24 to 48 hours, although read-out can also take place periodically, for instance once per week or per month.

The read-out of the thrombosis factors can then be carried out herein at longer intervals than the periodicity of the performance of the measurement. It can thus for instance be envisaged that once a day determined thrombosis factors are read out once per week or once per two weeks or once per month. That the device must be provided for this purpose with suitable memory means realizable with known means from the prior art will be apparent.

It is further pointed out that the determining of the stated factors can take place outside the implanted device. It is also conceivable to read out both the factors and the measured impedance values from which the factors are determined. Reading out can take place remotely with per se known techniques which are already known as such in the field of pacemakers.

It is possible here to envisage for instance radiographic read-out. According to the invention patients with a pacemaker are envisaged in the first instance, since most of these patients have atherosclerosis and the pacemaker system with its power source and its catheter ("lead") in the bloodstream can thus be easily modified for an electric impedance measurement of the blood. According to the invention however, this impedance measurement technique can also be applied wholly separately of a pacemaker, permanently using a separate measuring device or temporarily via a catheter in a peripheral vein to the right-hand atrium, as described above for monitoring an anti-coagulation therapy in acute thrombotic events.

Figure 2:
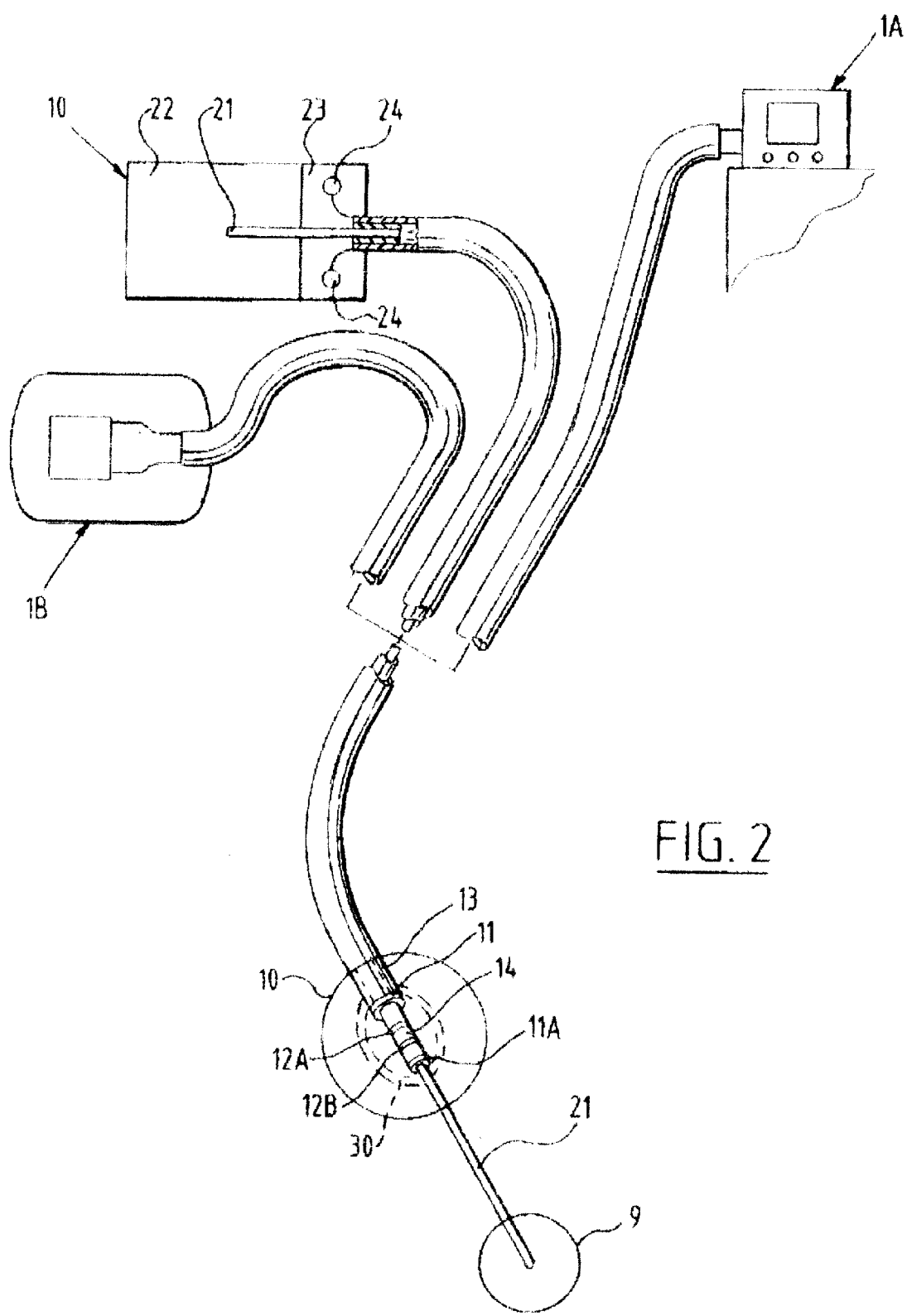

The present invention will be elucidated hereinbelow with reference to the drawing. Herein:

FIG. 1 shows a highly schematic, partly cut-away view of a human heart provided with a device according to the invention in three embodiments; and FIG. 2 shows a schematic, perspective cross-sectional view of a so-called "lead". Designated with 1 in FIG. 1 is the impedance measuring device, for temporary use (1A), for permanent use (1B) and combined (1C) with a heart pacemaker unit; with 2 the catheter or so-called lead; with 3 a human heart; with 4 the right-hand atrium; with 5 the right-hand ventricle; with 6 the sino-atrial node; with 7 the atrioventricular node; with 8 the bundle of His; with 9 a debouchment area of the bundle of His, particularly the debouchment area of the bundle of His at right-hand ventricle 5; with 10 an area of the lead 2, which area 10 comprises two electrodes for an intravascular impedance measurement and which is also specified in the terminology of the claims as the intravascular part; with 17 the hollow vena cava; with 18 the left-hand atrium; and with 19 the left-hand ventricle. FIG. 2 shows the connection of the actual pacemaker "lead" 21, also referred to as core wire and known from the pacemaker art, to the actual part 22 of heart pacemaker unit 1C.

Also shown schematically is that a separate part 23 of the heart pacemaker unit is intended for a separate power source with preferably a separate circuit for impedance measurement with connections 24 for the four impedance electrodes (two outer alternating current electrodes and two inner measuring electrodes). FIG. 2 further shows a schematic cross-section of catheter 2. The four impedance electrodes are situated in a circle round the actual pacemaker lead 21 and are separated in electrically insulated manner from this lead 21 and from each other and from the blood. The alternating current electrode 11A is connected to an insulating coax layer 14 and is in free connection with blood in the right-hand atrium. The other alternating current electrode 11B is connected to another electrically insulating coax layer 13 and is likewise in free connection with blood in the right-hand atrium, although it is located several mm higher (upstream) in the right-hand atrium. Between both ring electrodes an alternating current is sent with a frequency between 4 and 2000 kHz and an intensity of a maximum of 10 microAmpere/kHz. The alternating current can have a varying frequency or a number of superimposed frequencies. It preferably comprises a low and at least two high frequencies. The impedance is measured between the two measuring electrodes 12A and 12B. The effective blood volume of which the impedance is measured is designated schematically with 30 and is no greater than 4–5 mm at a distance used between the electrodes of 1 mm and a thickness of the electrodes of ½ mm. The surrounding tissue hereby causes a minimal interference.

The impedance measurement can be both a capacitive measurement and a resistance measurement. It is also possible to perform a phase difference measurement. Both coax layers 13, 14 of impedance electrodes 11, 12 are situated round the actual lead 21 and can slide relative thereto.

For this purpose both coax layers 13, 14 are received in a sheath which can slide relative to core wire 21 (or the actual lead 21). It is the intention that a catheter for a device according to the invention comprises an intravascular part with at least two electrode systems for an impedance measurement which with an end are electrically connectable to the measuring unit, and comprises one or more sensor electrodes and/or stimulating electrodes for the pacemaker function. After implantation of catheter 2 the ring electrodes 11, 12 lie distally close to the end of the core wire 21 in the right-hand ventricle. The ring electrodes 11, 12 are visible by examination with for instance X-rays. After fixation of core wire 21 in the apex of the right-hand ventricle, ring electrodes 11, 12 can be proximally retracted via the ends to that desired height in the right-hand atrium, wherein both ring electrodes 11, 12 "float" freely in the blood and good impedance signals can be recorded between the ring electrodes 11, 12 situated several mm from each other. In this manner ring electrodes can be positioned in the right-hand atrium by means of X-ray examination and adapted to the varying anatomy in each different individual. The concept of impedance electrodes as movable sheath round the actual pacemaker lead makes it possible that the normal pacemaker lead known from the pacemaker art can continue to be used with separately supplied impedance electrodes as sheaths therearound. The connection of the pacemaker lead to the pacemaker unit does not change in principle either. The pacemaker unit itself, however, must of course be modified to enable performing of impedance measurements.

It is further very well conceivable for device 1 to be adapted to perform electrical resistance measurements and/or electrical capacitance measurements at optionally successively differing voltage levels and/or current levels. On the basis of the performed electrical resistance measurements and/or electrical capacitance measurements, whether or not at varying voltage or amperage levels, device 1 is then able to determine the factors which are a measure for the tendency to thrombosis and for the inflammatory activity in atherosclerosis.

For this purpose the measurement signal generated for a determined period is processed such that variations therein with a frequency in the order of magnitude of the heart frequency are removed therefrom. Influences on the measured impedance caused by the intermittent flow of the blood resulting from the heart action will thus not be taken into account.

Removal of the undesired variations can for instance take place with analog or digital filtering techniques.

The determining of the factors will take place on the basis of predetermined reference tables, predetermined mathematical equations, models or otherwise. If sufficient experimental measurements are performed beforehand for this purpose, tables, equations and/or models can then be made for determining these said factors which are incorporated into the pacemaker unit using so-called chips and so on.

What is claimed is:

1. Method for determining properties of blood of a person, comprising:
    generating in vivo for a determined time, longer than a cardiac cycle, using an electrical alternating current of a determined frequency, a measurement signal of the impedance of the blood between at least two points centrally in a blood volume, said blood volume having a boundary;
    processing the measurement signal such that variations therein with a frequency in the order of magnitude of the heart frequency are filtered therefrom; and
    determining the properties of the blood from the processed measurement signal using predetermined relations between impedance and the properties of the blood.

2. Method as claimed in claim 1, generating an ECG signal which is recorded in a cavity containing the blood volume, and processing of the measurement signal takes place by considering only measurement values in the same phase each time of the ECG signal.

3. Method as claimed in claim 1, which includes administering a blood viscosity-reducing agent to the person prior to generating said measurement signal in a dosage such that the measured impedance is adjusted to a predetermined value.

4. Method as claimed in claim 1, wherein the distance between said at least two points is a small fraction of the distance of these points to a boundary of the blood volume.

5. Method as claimed in claim 1, which includes selecting a central location in the right-hand atrium of the heart for said at least two points centrally in a blood volume.

6. Device for determining determined blood properties of a person, comprising a catheter, which comprises at least two electrode systems close to a distal end and connecting lines extending from the electrode systems to the proximal end of the catheter, a measuring device which is connectable to the connecting lines and which is embodied such that it can generate a measurement signal of the impedance between the electrode systems for a period of time longer than a cardiac cycle, and a processing device which is embodied such that it processes the measurement signal such that variations therein with a frequency in the order of magnitude of the heart frequency are filtered therefrom and determining properties of the blood from the filtered measurement signal.

7. Device as claimed in claim 6, characterized in that the measuring device generates an ECG signal and that the processing device records measurement signals in each case during at least one determined phase of the ECG signal.

8. Device as claimed in claim 7, characterized in that the determined phase corresponds with the occurrence of the maximal and/or the minimal impedance.

9. Device as claimed in any of the claims 5–8, characterized in that the at least two electrode systems comprise at least two electrodes which are connectable to the alternating current and two measuring electrodes lying therebetween.

10. Device as claimed in any of the claims 5–9, characterized in that the electric alternating current is adjusted to a frequency between 4 and 2000 kHz.

11. Device as claimed in any of the claims 5–10, characterized in that the processing device is further adapted to determine a factor subject to the measured impedance, which factor is a measure for the tendency to thrombosis.

12. Device as claimed in any of the claims 5–11, characterized in that the processing device is further adapted to determine a factor subject to the measured impedance, which factor indicates the inflammatory activity in atherosclerosis.

13. Device as claimed in any of the foregoing claims, characterized in that the impedance measurement is a resistance measurement and/or capacitance measurement and/or a phase difference measurement.

14. Device as claimed in any of the foregoing claims, characterized in that the measuring device is received in an implantable unit.

15. Device as claimed in any of the foregoing claims, characterized in that the measuring device is combined with an implantable heart pacemaker unit and is provided with two electrically separated circuits each having an individual power source, wherein the one circuit is adapted for the pacemaker function and the other circuit is adapted for the impedance measurement.

16. Device as claimed in any of the foregoing claims, characterized in that the catheter is embodied such that the at least two electrode systems for performing the impedance measurement can be placed in the right-hand atrium of the heart.

17. Device as claimed in any of the foregoing claims, characterized in that it comprises a catheter which is electrically connectable to the pacemaker unit with its proximal end and comprises one or more sensor electrodes and/or stimulating electrodes for the pacemaker function.

18. Device as claimed in claim 17, characterized in that the sensor electrodes and/or stimulating electrodes for the pacemaker function are arranged on the distal side relative to the electrode systems for the impedance measurement, that the outermost distal end of the catheter is intended for placing in the apex of the right-hand ventricle, and that the distance between the outermost distal end of the catheter and the electrode systems for the impedance measurement is such that, when the outermost distal end is placed in the apex of the right-hand ventricle, the electrode systems for the impedance measurement are situated centrally in the right-hand atrium.

19. Device as claimed in claim 17, characterized in that the electrode systems for the impedance measurement are arranged on a sheath round a core wire to the sensor electrodes and/or stimulating electrodes and that this sheath is slidable along the core wire.

20. Device as claimed in any of the foregoing claims, characterized in that it is adapted to enable remote read-out of the determined factors of thrombosis formation and/or of inflammatory activity and/or the measured impedance values.

21. Catheter for a device as claimed in any of the foregoing claims, characterized in that this catheter comprises an intravascular part with at least two electrode systems for an impedance measurement, is electrically connectable with one end to the pacemaker unit, and comprises one or more sensor electrodes and/or stimulating electrodes for the pacemaker function.

22. Catheter as claimed in claim 21, characterized in that the sensor electrodes and/or stimulating electrodes for the pacemaker function are arranged on the distal side relative to the electrode systems for the impedance measurement, that the outermost distal end of the catheter is intended for placing in the apex of the right-hand ventricle, and that the distance between the outermost distal end of the catheter and the electrode systems for the impedance measurement is such that, when the outermost distal end is placed in the apex of the right-hand ventricle, the electrode systems for the impedance measurement are situated in the right-hand atrium.

* * * * *